(12) United States Patent
Grison et al.

(10) Patent No.: US 12,096,770 B2
(45) Date of Patent: Sep. 24, 2024

(54) METHOD FOR PREPARING AN INSECT REPELLENT AGENT

(71) Applicants: CENTRE NATIONAL DE LA RECHERCHE SCIENTIFIQUE, Paris (FR); UNIVERSITÉ DE MONTPELLIER, Montepellier (FR)

(72) Inventors: Claude Grison, Castelnau le Lez (FR); Andrii Stanovych, Jacou (FR)

(73) Assignees: CENTRE NATIONAL DE LA RECHERCHE SCIENTIFIQUE (CNRS), Paris (FR); UNIVERSITE DE MONTPELLIER, Montpellier (FR)

( * ) Notice: Subject to any disclaimer, the term of this patent is extended or adjusted under 35 U.S.C. 154(b) by 249 days.

(21) Appl. No.: 17/625,928

(22) PCT Filed: Jul. 10, 2020

(86) PCT No.: PCT/EP2020/069568
§ 371 (c)(1),
(2) Date: Jan. 10, 2022

(87) PCT Pub. No.: WO2021/005214
PCT Pub. Date: Jan. 14, 2021

(65) Prior Publication Data
US 2022/0248669 A1    Aug. 11, 2022

(30) Foreign Application Priority Data

Jul. 10, 2019 (FR) ........................... 1907753

(51) Int. Cl.
| C07C 29/56 | (2006.01) |
| A01N 27/00 | (2006.01) |
| A01N 31/02 | (2006.01) |
| A01N 31/04 | (2006.01) |
| A01N 31/06 | (2006.01) |

(Continued)

(52) U.S. Cl.
CPC ............ *A01N 31/06* (2013.01); *A01N 27/00* (2013.01); *A01N 31/02* (2013.01); *A01N 31/04* (2013.01); *A01P 17/00* (2021.08); *C07C 29/56* (2013.01); *C07C 29/86* (2013.01); *C07C 2601/14* (2017.05)

(58) Field of Classification Search
CPC ......... C07C 29/56; C07C 29/86; A01N 31/06; A01N 27/00; A01P 17/00
See application file for complete search history.

(56) References Cited

U.S. PATENT DOCUMENTS

2006/0270737 A1    11/2006 Matias

FOREIGN PATENT DOCUMENTS

| CN | 106380377 A | * | 2/2017 |
| WO | 9202136 A1 | | 2/1990 |
| WO | 2009034352 A1 | | 3/2009 |

OTHER PUBLICATIONS

Jeremy Drapeau et al, "Green synthesis of para-Menthane-3,8-diol from Eucalyptus citriodora: Application for repellent products", Comptes Rendus Chimie, vol. 14, No. 7-8, Jul. 1, 2011 (Jul. 1, 2011), p. 629-635.

(Continued)

*Primary Examiner* — Sikarl A Witherspoon
(74) *Attorney, Agent, or Firm* — WC&F IP

(57) ABSTRACT

The present invention relates to a method for preparing p-menthane-3,8-diol, characterised in that it comprises the following steps:

a. preparation of an aqueous solution comprising between 0.05% and 5% by mass, preferably between 0.05% and 2% by mass, preferentially between 0.05% and 1% by mass, even more preferentially between 0.05% and 0.5% by mass of an ammonium salt, the said ammonium salt being characterised in that it is selected from the group formed by an amino acid ammonium salt, and in particular an amino acid hydrochloride, a vitamin B ammonium salt, and in particular a vitamin B hydrochloride, an ammonium salt of an amino acid ester, and an ammonium salt of a vitamin B ester, or is defined by the following formula (I):

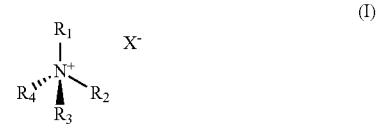

wherein $R_1$ represents a benzyl, optionally substituted, or $R_1$ represents an alkyl, either linear or branched, optionally cyclical, saturated or unsaturated, optionally substituted, comprising from 1 to 10 carbon atoms, preferably from 1 to 6 carbon atoms, preferentially from 2 to 4 carbon atoms, and $R_2$, $R_3$ and $R_4$ represent a hydrogen or a methyl group, and X represents a chlorine atom, bromine atom or an OR' group, R' being an alkyl group comprising from 1 to 10 carbon atoms, b. adding of citronellal to the aqueous solution obtained in the step a), and obtaining a mixture;

c. stirring and heating of the mixture obtained in the step b);

d. decanting of the reaction medium obtained at the end of step c) and obtaining at least two phases; and e. separation of the said at least two phases obtained in the step d), and obtaining at least one aqueous phase and at least one organic phase, the said organic phase comprising at least p-menthane-3,8-diol.

20 Claims, 1 Drawing Sheet

(51) Int. Cl.
*A01P 17/00* (2006.01)
*C07C 29/86* (2006.01)

(56) References Cited

OTHER PUBLICATIONS

Gúnter C. Müller et al, "Efficacy of the botanical repellents geraniol, linalool, and citronella against mosquitoes", Journal of Vector Ecology,vol. 34, No. 1, Jun. 1, 2009 (Jun. 1, 2009), p. 2-8.
Teun Dekker et al, "Identification of mosquito repellent odours from Ocimum forskolei", Parasites & Vectors, Biomed Central Ltd, London UK,vol. 4, No. 1, Sep. 22, 2011 (Sep. 22, 2011), p. 183.
Charles L. Cantrell et al, "Isolation and identification of mosquito biting deterrents from the North American mosquito repelling folk remedy plant, *Matricaria discoidea* DC.", PLOS One,vol. 13, No. 10, Oct. 31, 2018 (Oct. 31, 2018), p. e0206594.

* cited by examiner

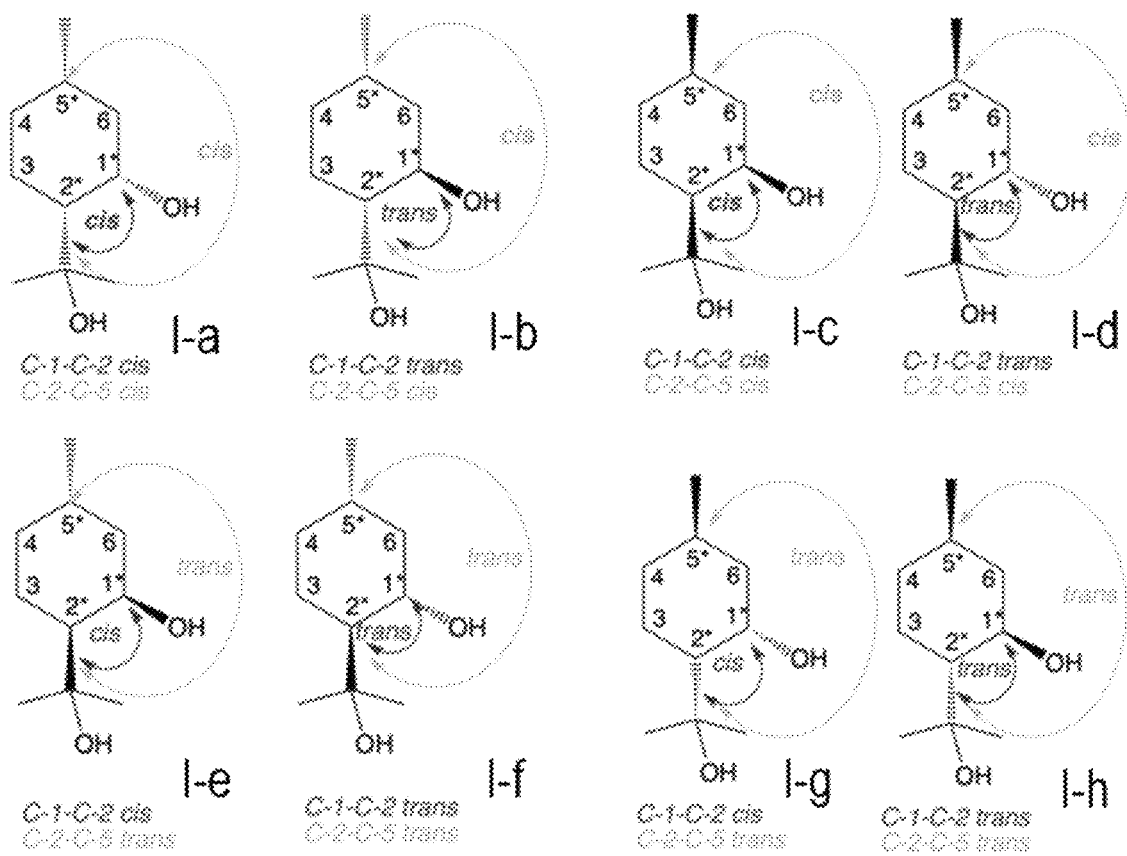

METHOD FOR PREPARING AN INSECT REPELLENT AGENT

The present invention relates to a novel method of synthesis for synthesising an insect repellant agent, in particular p-menthane-3,8-diol.

The present invention also relates to a composition comprising an insect repellent agent, in particular p-menthane-3,8-diol; as well as the use of this composition as an insect repellent agent, in particular for repelling mosquitoes.

STATE OF THE ART

The globalisation of trade and international passenger travel, is a major cause behind the widespread introduction of invasive insects. Thus, over the last decades, the geographical distribution of hematophagous (or blood-feeding) arthropods, and in particular of mosquitoes carrying vector-borne diseases, has increased considerably. Such insects represent a major health problem insofar as they transmit pathogenic agents believed to cause alarming epidemics.

Among these invasive insects, the tiger mosquito, or *Aedes albopictus*, accidentally imported from Southeast Asia, has found favourable breeding grounds in Europe, China and the Indian Ocean. The adaptability of this mosquito species is particularly worrying, because it is a potential vector of 20 disabling, and indeed even fatal diseases such as chikungunya, dengue and zika.

In the absence of vaccines for the majority of mosquito-borne diseases, the use of repellent agents is the primary measure for avoiding human-mosquito contact.

There currently exist two types of repellents: synthetic agents and natural products.

Synthetic repellents are the most widely used anti-mosquito insect repellents. The synthetic agent that is most highly active against the tiger mosquito is DEET or N,N diethyl-meta-toluamide. However, while its efficacy has been acknowledged, so too has its toxicity for the nervous system. It inhibits acetylcholinesterase, an enzyme that is essential to the cholinergic synaptic transmission of insects as also of mammals (Corbel et al., 2009). This effect is to be compared to that of organophosphate pesticides or carbamates; and repeated use of DEET in combination with other substances is not recommended for children under 12 years of age and pregnant women.

These concerns about consumer safety and mosquito resistance to these synthetic repellents have led to a growing demand for natural alternatives.

Among the many existing natural products, only p-menthane-3,8-diol (PMD) has a significant repellent activity of interest. A 20% formulation of PMD has been shown to provide 7 to 8 hours of protection against *Aedes albopictus*, similar to a product containing 15% DEET (Barnard DR, Xue R-D (2004) Laboratory evaluation of mosquito repellents against *Aedes albopictus, Culex nigripalpus*, and *Ochlerotatus triseriatus* (Diptera: Culicidae). J Med Entomol 41(4):726-730), while also having low toxicity and no adverse effects, except for eye irritation, which is observed for all natural non-toxic active ingredients.

This organic compound may be extracted from the essential oil of lemon scented eucalyptus (Corymbia citriodora), which is a species endemic to Australia. However, a limited amount (of the order 1%) of PMD is present in this essential oil. Given the restricted geographical distribution of *Eucalyptus citriodora*, the development of natural production of PMD is unable to satisfy the market demand. This is why the majority of PMDs used in repellents are derived from synthetic processes.

PMD can be synthesised from an abundantly occurring natural raw material: citronellal. This synthesis comprises of two steps: 1) the intramolecular ene-carbonyl reaction of citronellal to give isopulegol, followed by 2) the addition of $H_2O$ to the intermediate isopulegol.

A number of studies relating to this synthesis have been carried out.

For example, the patent U.S. Pat. No. 5,959,161 describes the aqueous phase synthesis of PMD in the presence of sulfuric acid $H_2SO_4$ from citronellal. A number of variants have also been proposed in order to promote the production of the cis stereoisomer of PMD, reputed to have better repellent activity than the trans stereoisomer (WO 9202136).

On the other hand, the synthesis of PMD catalysed by a Lewis acid has been less studied, because it is significantly less efficacious. For example, the use of $Mo(CO)_5OTf)_2$ in dimethoxyethane (DME) has been described (J. Org. Chem. 1999, 64, 2765-2775). After a period of 48 hours, 80% cis stereoisomers of PMD had been obtained; however the preparation of the catalytic complexes used in these syntheses is a delicate process that is also dangerous and expensive.

Thus, in general, the methods of production for producing synthetic PMD involve the use of corrosive reagents, such as $H_2SO_4$, and/or the use of toxic solvents such as dichloromethane, toluene, benzene or DME, as well as neutralisation and/or purification steps that generate waste.

Thus for this reason, the use of natural catalysts has also been tested in order to develop more ecologically friendly processes and methods.

EP2862442 describes, for example, the use of citric acid as a catalyst for the reaction to convert citronellal into PMD. However, the solubility of the carboxylic acids in the organic phase necessitated a final treatment of the reaction mixture, which generated waste (solvent and inorganic salts). This neutralisation step resulted in a Sheldon's environmental factor (ratio of the mass of waste to the obtained mass of desired product) that was unsatisfactory from an ecological standpoint.

Thus, although some syntheses that make it possible to obtain PMD are bio-inspired, the qualification of "natural" attributed to the PMD obtained according to these methods is very often questionable, because if they were to be carefully examined, it could well be noted that these methods are far from being respectful of the environment.

DESCRIPTION OF THE DRAWING FIGURE

FIG. 1 schematically presents eight stereoisomers of p-menthane-3,8-diol (PMD).

AIMS OF THE INVENTION

Thus, there is a need to provide a repellent preparation method for preparing a repellent agent that repels hematophagous (or blood-feeding) arthropods, and in particular mosquitoes, which addresses one or more of the above-noted technical problems; and particularly to provide a repellent preparation method for preparing a repellent agent that repels haematophagous arthropods, and in particular mosquitoes, which is more environmentally respectful, safer and efficient as compared to existing preparation methods.

There is also a need to provide a composition comprising an insect repellent agent, in particular p-menthane-3,8-diol, which is efficacious for repelling hematophagous arthropods, and in particular mosquitoes, notably the tiger mosquito.

Thus, an objective of the present invention is to provide a method that makes it possible to prepare p-menthane-3,8-diol in an efficient manner and which serves to ameliorate its impact from an ecological standpoint.

Another objective of the present invention is to provide a composition that comprises in particular p-menthane-3,8-diol, and to provide a composition that can be used as a repellent agent against hematophagous arthropods, in particular mosquitoes, the said repellent agent being more efficacious than those of the state of the art.

DETAILED DESCRIPTION OF THE INVENTION

The present invention relates to a preparation method for preparing p-menthane-3,8-diol, characterised in that it comprises the following steps:

a. preparation of an aqueous solution comprising between 0.05% and 5% by mass, preferably between 0.05% and 2% by mass, preferentially between 0.05% and 1% by mass, even more preferentially between 0.05% and 0.5% by mass of an ammonium salt, the said ammonium salt being characterised in that it is selected from the group formed by an amino acid ammonium salt, and in particular an amino acid hydrochloride, a vitamin B ammonium salt, and in particular a vitamin B hydrochloride, and any one of the derivatives thereof, in particular an ammonium salt of an amino acid ester, or an ammonium salt of a vitamin B ester, or is defined by the following formula (I):

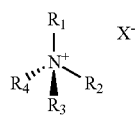

(I)

wherein $R_1$ represents a benzyl, optionally substituted, or $R_1$ represents an alkyl, either linear or branched, optionally cyclical, saturated or unsaturated, optionally substituted, comprising from 1 to 10 carbon atoms, preferably from 1 to 6 carbon atoms, preferentially from 2 to 4 carbon atoms, and $R_2$, $R_3$ and $R_4$ represent a hydrogen or a methyl group, and X represents a chlorine atom, bromine atom or an OR' group, R' being an alkyl group comprising from 1 to 10 carbon atoms;

b. adding of citronellal to the aqueous solution obtained in step a), and obtaining a mixture;

c. stirring and heating of the mixture obtained in step b);

d. decanting of the reaction medium obtained at the end of step c) and obtaining at least two phases; and e. separation of the said at least two phases obtained in step d), and obtaining at least one aqueous phase and at least one organic phase, the said organic phase comprising at least p-menthane-3,8-diol.

Preferably, $R_1$ represents an alkyl, either linear or branched, optionally cyclical, saturated or unsaturated, optionally substituted, comprising from 1 to 10 carbon atoms, preferably from 1 to 6 carbon atoms, preferentially from 2 to 4 carbon atoms.

Within the meaning and scope of the present invention, p-menthane-3,8-diol (PMD) corresponds to (2-hydroxypropan-2-yl)-5-methylcyclohexan-1-ol, in the form of at least one of its stereoisomers or any one of the mixtures thereof.

PMD exists in the form of eight stereoisomers I-a, I-b, I-c, I-d, I-e, I-f, I-g, and I-h.

According to the invention, the cis isomers of PMD correspond to a mixture of stereoisomers of PMD comprising at least one stereoisomer selected from the stereoisomers I-a, I-c, I-e and I-g.

According to the invention, the trans stereoisomers of PMD correspond to a mixture of stereoisomers of PMD that comprise at least one stereoisomer selected from the stereoisomers I-b, I-d, I-f and I-h.

According to the invention, an amino acid is a compound that comprises both at least one carboxylic acid functional group —COOH, and at least one primary amine functional group —NH$_2$, or at least one secondary amine functional group —NH—.

According to the invention, a vitamin B is one of the following eight vitamins: vitamin B1 also known as thiamine, vitamin B2 also known as riboflavin, vitamin B3 also known as niacin, vitamin B5 also known as pantothenic acid, vitamin B6 also known as pyridoxine, vitamin B8 also known as biotin, vitamin B9 also known as folic acid, and vitamin B12 also known as cobalamins.

According to the invention, an ammonium salt is an ionic compound that comprises an anion X$^-$ and a cation comprising at least one cationic functional group —$^+$NH$_3$ or —$^+$NH$_2$—, with X representing a chlorine atom, bromine atom, or an OR' group, R' being an alkyl group comprising from 1 to 10 carbon atoms.

Preferably, the ammonium salt is selected from the group consisting of an amino acid ammonium salt and a vitamin B ammonium salt.

In an advantageous manner, the amino acid ammonium salt is an amino acid hydrochloride.

In an advantageous manner, the vitamin B ammonium salt is vitamin B hydrochloride.

Within the meaning and scope of the present application, the term "hydrochloride" is understood to refer to a substance that combines one or more molecules of hydrogen chloride.

According to the invention, an amino acid hydrochloride is an ionic compound that comprises an anion Cl$^-$ and a cation comprising an amino acid, the said amino acid comprising at least one primary amine functional group —NH$_2$, or at least one secondary amine functional group —NH— in the form of —$^+$NH$_3$ or —$^+$NH$_2$—.

According to the invention, a vitamin B ammonium salt is an ionic compound in which at least one primary amine functional group —NH$_2$ or at least one secondary amine functional group —NH— of vitamin B is in the form of a cation.

According to the invention, the term "derivative" is understood to refer in particular to organic derivatives, and in particular to compounds that substantially retain the activity of the compound from which they are derived.

Preferably, the amino acid ammonium salt derivative is an ammonium salt of an amino acid ester. An amino acid ester is defined as an amino acid that comprises at least one ester functional group, the said ester functional group being obtained by esterification of at least one carboxylic acid functional group of the said amino acid.

Preferably, the derivative of the vitamin B ammonium salt is an ammonium salt of vitamin B ester. A vitamin B ester is defined as a vitamin B that comprises at least one ester functional group, the said ester functional group being obtained by esterification of at least one carboxylic acid functional group of the said vitamin B.

Preferably, the compound having the formula (I) is betaine hydrochloride.

Within the meaning and scope of the present invention, the term "betaine" is understood to refer to a zwitterionic compound in which the nitrogen atom carrying the positive charge does not bear a hydrogen atom and is not adjacent to the atom carrying the negative charge.

Preferably, the betaine is 2-trimethylammonioacetate (CAS: 107-43-7).

Within the meaning and scope of the present invention, citronellal corresponds to 3,7-dimethyloct-6-en-1-al (CAS number: 106-23-0), in one of its two enantiopure forms or as a racemic mixture.

Preferably, the step c) of the method according to the invention is carried out at a temperature comprised between 50° C. and 90° C., preferably between 60° C. and 80° C., for example for a period of between 30 minutes and 10 hours, preferably between 1 hr and 8 hrs.

According to an alternative or in addition, step c) of the method according to the invention is carried out under ultrasound, at a frequency of between 20 Hz and 60 Hz.

Preferably, the method according to the invention is characterised in that the amino acid ammonium salt derivative comprises at least one COOR ester functional group, R being an alkyl, either linear or branched, comprising from 1 to 10 carbon atoms, preferably from 1 to 5 carbon atoms, preferably R is a methyl group.

In a preferential manner, the method according to the invention is characterised in that an amino acid ammonium salt is selected from among hydrochlorides of histidine, guanine and glycine, preferably from among hydrochlorides of histidine and glycine.

Within the meaning and scope of the present invention, histidine corresponds to 2-amino-3-(1H-imidazol-4-yl)propanoic acid, in one of its two enantiopure forms or as a racemic mixture.

Within the meaning and scope of the present invention, guanine corresponds to 2-amino-1,9-dihydro-6H-purin-6-one (CAS number: 73-40-5).

Within the meaning and scope of the present invention, glycine corresponds to 2-aminoethanoic acid (CAS number: 56-40-6).

Preferably, the method according to the invention is characterised in that the group $R_1$ is a saturated linear alkyl group, comprising from 1 to 10 carbon atoms, and further comprising a carboxylic acid functional group, preferably in the terminal position of the said alkyl group.

Preferably, $R_1$ is a saturated linear alkyl group comprising from 1 to 6 carbon atoms, preferentially from 1 to 3 carbon atoms, and further comprises a carboxylic acid functional group, preferably in the terminal position of the said alkyl group.

In an advantageous manner, $R_1$ is an ethyl group comprising a carboxylic acid functional group in the terminal position.

In a preferred manner, the method according to the invention is characterised in that the ammonium salt is selected from among histidine O-methyl dihydrochloride, guanine hydrochloride, glycine O-methyl hydrochloride, vitamin B1 dihydrochloride, vitamin B6 hydrochloride, and 2-trimethylammonioacetate hydrochloride.

According to a first embodiment, the ammonium salt is selected from among histidine O-methyl dihydrochloride (H) and glycine O-methyl hydrochloride (G) having the following formula:

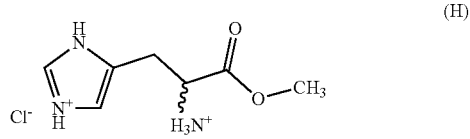

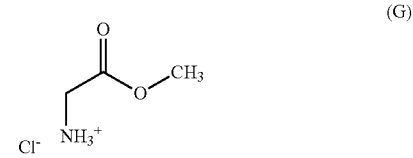

According to another embodiment, the ammonium salt is vitamin B1 dihydrochloride (V) having the following formula:

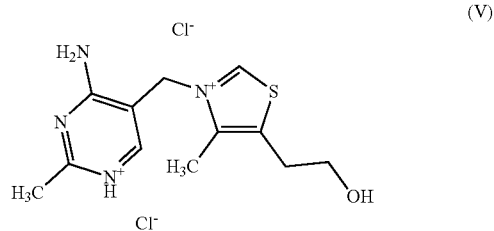

According to yet another embodiment, the ammonium salt is betaine hydrochloride (B) having the following formula:

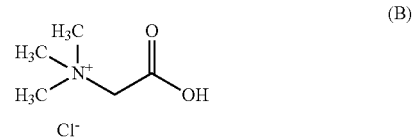

Preferably, the method according to the invention is characterised in that the citronellal is used in the form of an essential oil, preferably selected from the group consisting of essential oils derived from the species: *Eucalyptus citriodora, Cymbopogon winternianus, Melissa officinalis* or *Citrus hystix*, preferably derived from the species *Eucalyptus citriodora, Cymbopogon winternianus* or *Citrus hystix*.

Within the meaning and scope of the present application, the term "essential oil" is understood to refer to a volatile odorous substance produced by certain plants and which is able to be extracted, preferably by hydrodistillation, in the form of a liquid.

In an advantageous manner, the method according to the invention is characterised in that the organic phase obtained at the end of step e) further comprises at least one compound selected from citronellal, isopulegol and an acetal, the said acetal being produced by reaction between citronellal and p-menthane-3,8-diol.

Within the meaning and scope of the present invention, isopulegol corresponds to 5-methyl-2-prop-1-en-2-ylcyclohexan-1-ol, in the form of at least one of its stereoisomers or any one of the mixtures thereof.

Within the meaning and scope of the present invention, an acetal is a compound produced by an acetalisation reaction between the aldehyde functional group of citronellal and the two hydroxyl functional groups of PMD.

Preferably, the acetal corresponds to the compound (Ac) having the following formula:

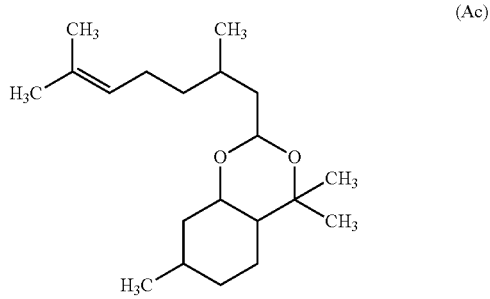 [SMILES: CC(C)=CCCC(C)CC1OC2CC(C)CCC2C(C)(C)O1]

(Ac)

in the form of at least one of its stereoisomers or any one of the mixtures thereof.

In an even more advantageous manner, the method according to the invention is characterised in that the organic phase obtained at the end of step e) further comprises at least one compound selected from linalool, citronellol and geraniol.

Within the meaning and scope of the present invention, linalool corresponds to the compound 3,7-dimethylocta-1,6-dien-3-ol, in one of its two enantiopure forms or as a racemic mixture.

Within the meaning and scope of the present invention, citronellol corresponds to 3,7-dimethyloct-6-en-1-ol (CAS number: 106-22-9) in one of its two enantiopure forms or as a racemic mixture.

Within the meaning and scope of the present invention, geraniol corresponds to trans-3,7-dimethyl-2,6-octadien-1-ol (CAS number: 106-24-1).

Preferably, the method according to the invention further comprises a step f) of adding at least one compound selected from citronellol, geraniol, terpineol and caryophyllene to the organic phase comprising p-menthane-3,8-diol obtained in the step e).

Within the meaning and scope of the present invention, terpineol corresponds to the compound 2-(4-methyl-1-cyclohex-3-enyl)propan-2-ol, in the form of at least one of its stereoisomers or any one of the mixtures thereof.

Within the meaning and scope of the present invention, caryophyllene corresponds to (1R,4E,9S)-4,11,11-trimethyl-8-methylidenebicyclo[7.2.0]undec-4-ene.

According to a particular embodiment, the method according to the invention is characterised in that it further comprises a step f) of adding at least one compound selected from terpineol and caryophyllene to the organic phase comprising p-menthane-3,8-diol obtained in the step e).

According to another particular embodiment, the method according to the invention is characterised in that it further comprises a step f) of adding citronellol and geraniol to the organic phase comprising p-menthane-3,8-diol obtained in the step e).

According to one embodiment, the method of the invention is carried out in the absence of any strong acid.

The term "strong acid" is understood to refer to an acid which, in aqueous solution, completely dissociates into H+ ions and into a weak base, known as the conjugate base of the acid. A strong acid has a pKa with a value less than or equal to 0. By way of example, sulfuric acid, sulfonic acid, hydrochloric acid, and nitric acid are strong acids.

The present invention also relates to a composition obtainable by the method according to the invention, characterised in that it comprises at least p-menthane-3,8-diol, and optionally at least one compound selected from citronellal, isopulegol, and an acetal, the said acetal being produced by reaction between citronellal and p-menthane-3,8-diol.

Preferably, the composition according to the invention comprises:
from 35 to 100 mole %, preferably from 50 to 99 mole %, preferentially from 70 to 98 mole % of p-menthane-3,8-diol; and optionally
from 0.1 to 40 mole %, preferably from 0.5 to 20 mole %, preferentially from 1 to 10 mole % of citronellal; and optionally
from 1 to 30 mole %, preferably from 1 to 20 mole %, preferentially from 1 to 15 mole % of isopulegol; and optionally
from 0.1 to 20 mole %, preferably from 0.5 to 10 mole %, preferentially from 1 to 5 mole % of acetal.

Preferentially, the composition according to the invention comprises: at least 70 mole % of p-menthane-3,8-diol relative to the total number of moles of the composition; citronellal and an acetal; and optionally isopulegol; the said acetal being produced by reaction between citronellal and p-menthane-3,8-diol.

In an advantageous manner, the composition according to the invention comprises from 70 to 98 mole % of p-menthane-3,8-diol relative to the total number of moles of the composition.

In an even more advantageous manner, the composition according to the invention comprises, relative to the total number of moles of the composition:
from 70 to 98 mole % of p-menthane-3,8-diol;
from 0.1 to 40 mole %, preferably from 0.5 to 20 mole %, preferentially from 1 to 10 mole % of citronellal;
from 0.1 to 20 mole %, preferably from 0.5 to 10 mole %, preferentially from 1 to 5 mole % of acetal; and optionally
from 1 to 30 mole %, preferably from 1 to 20 mole %, preferentially from 1 to 15 mole % of isopulegol.

Preferably, the composition according to the invention is characterised in that the p-menthane-3,8-diol is present in the form of at least one of its stereoisomers.

The stereoisomers of p-menthane-3,8-diol are as defined here above.

Preferably, the composition according to the invention is characterised in that the p-menthane-3,8-diol is present in the form of a mixture of cis and trans stereoisomers, the said mixture comprising from 10 to 90 mole %, preferably from 20 to 80 mole % of cis stereoisomers, and from 10 to 90 mole %, preferably from 20 to 80 mole % of trans stereoisomers.

Preferably, the composition according to the invention further comprises from 0.1 to 10 mole %, preferably from 0.5% to 5 mole % of terpineol.

Preferably, the composition according to the invention further comprises from 0.1 to 10 mole %, preferably from 0.5% to 5 mole % of caryophyllene.

Preferably, the composition according to the invention further comprises from 0.1 to 15 mole %, preferably from 0.5% to 5 mole % of linalool.

Preferably, the composition according to the invention further comprises from 0.1 to 40 mole %, preferably from 1 to 30 mole %, preferentially from 2 to 20 mole % of citronellol.

Preferably, the composition according to the invention further comprises from 0.1 to 40 mole %, preferably from 1% to 35 mole % of geraniol.

The present invention also relates to the use of the composition according to the invention as a repellent agent that repels at least one insect.

The present invention also relates to the use of the composition according to the invention as a repellent agent that repels at least one hematophagous (or blood-feeding) arthropod.

Within the meaning and scope of the present invention, the term "repellent agent that repels at least one insect" is understood to refer to a compound or a composition that provides the ability to effectively keep an insect away from their "target" (humans or animals).

Within the meaning and scope of the present invention, the term "repellent agent that repels at least one hematophagous arthropod" is understood to refer to a compound or a composition that provides the ability to effectively keep a hematophagous (or blood-feeding) arthropod away from their "target" (humans or animals).

The repellant agent may be in the form of a lotion, cream, roll-on applicator, or a spray.

In a preferred manner, in the use of the composition according to the invention as a repellant agent for repelling at least one insect, the insect is selected from the group consisting of mosquitoes, ticks and midges.

In an advantageous manner, in the use of the composition according to the invention as a repellent agent that repels at least one insect, the insect is selected from mosquitoes, preferably from the genus Aedes, Anopheles, or Culex, preferably the mosquito species is Aedes albopictus.

In a preferred manner, in the use of the composition according to the invention as a repellent agent that repels at least one hematophagous arthropod, the hematophagous arthropod is selected from the group consisting of mosquitoes, ticks and midges.

In an advantageous manner, in the use of the composition according to the invention as a repellent agent that repels at least one hematophagous arthropod, the hematophagous arthropod is selected from mosquitoes, preferably from the genus Aedes, Anopheles, or Culex, preferably the mosquito species is Aedes albopictus.

The invention will now be described by making use of the following non-limiting examples.

EXAMPLES

The citronellal, ammonium salts (H), (G), (V) and (B), N,N diethyl-meta-toluamide (DEET), commercial cis/trans PMD 75/25 (derived from RS citronellal), caryophyllene, citronellol, geraniol and terpineol are acquired from Sigma-Aldrich.

The acetal having the formula (Ac), the commercial cis/trans PMDs 75/25 (derived from R citronellal, S citronellal), the cis PMD, the trans PMD, isopulegol were obtained by chromatographic separation of the mixture obtained by bringing about reaction between the citronellal and the ammonium salt (B).

The essential oils of Eucalyptus citriodora, Cymbopogon winteranius or Citrus hystrix are acquired from the Compagnie des Sens.

All of the essential oils are certified ORGANIC according to the COSMOS Organic standard by Ecocert Greenlife and guaranteed 100% pure, natural and whole.

Example 1: Production of PMD from Pure Citronellal

PMD may be produced from pure citronellal in the presence of an ammonium salt as defined according to the invention.

In order to do this, 2.5 mL of citronellal are added to 10 mL of an aqueous solution comprising between 0.05% and 0.4% by mass of an ammonium salt. The mixture is agitated for a period of 6 hours at 70° C., or for a period of 2 hours at 70° C. under ultrasound, and then decanted. The PMD is comprised in the organic phase, and the aqueous phase includes the ammonium salt.

The results obtained are presented in the following table:

TABLE 1

| Compo | Ammonium salt (mass %) | Reaction time (h) | T (° C.) | Conversion of citronellal (mole %) | % PMD in the organic phase at the end of the reaction (mole %) |
|---|---|---|---|---|---|
| 1.1 | (H) (0.4%) | 6 h | 70° C. | 100 | 87 |
| 1.2 | (G) (0.4%) | 6 h | 70 ° C. | 90 | 88 |
| 1.3 | (V) (0.4%) | 6 h | 70° C. | 95 | 85 |
| 1.4 | (B) (0.05%) | 6 h | 70° C. | 83 | 79 |
| 1.5 | (B) (0.2%) | 6 h | 70° C. | 98 | 89 |
| 1.6 | (B) (0.2%) | 30 min (+ultrasound) | 70° C. | 100 | 92 |

The method according to the invention involves catalysts in the form of ammonium salts, that have an ionic structure and are weakly acidic. Thanks to the method according to the invention, a simple decantation makes it possible to recover the PMD at a neutral pH, because the catalyst (the ammonium salt) is not soluble in the PMD (unlike carboxylic acids and sulfuric acids, for example). The method is very simple to implement because the treatment of the reaction medium is a simple decantation process. The yields and selectivity values are excellent. In addition, the reaction times are short compared to known methods (2 hrs - 6 hrs). Finally, no waste is produced, because the catalyst contained in the aqueous phase can be recycled and reused up to 10 times without significant loss of reactivity.

The recycling of the aqueous phase has been studied more particularly by using composition 1.5. At the conclusion of the reaction described with 0.2% betaine without ultrasonic activation, the two phases are separated. The organic phase, constituted of PMD, crystallises spontaneously. This result reflects the high degree of purity of the PMD obtained. The aqueous phase (10 mL) is isolated and recovered directly for a new synthesis, without treatment and without addition. It is directly subjected to the citronellal (2.5 mL) at 70° C. After 6 hours of reaction, the two phases are again separated. The organic phase, that is very rich in PMD, crystallises again. This phenomenon of spontaneous crystallisation of PMD is observed 8 consecutive times. The Gas Chromatography-Mass Spectrometry/Flame-Ionisation Detection (GC MS/FID) analyses confirm the stability of the composition of the organic medium. Beyond that, recycling remains possible under the same conditions and with the same efficiency, but the PMD is obtained in the form of a yellowish viscous oil. The results are shown in the following table.

TABLE 2

| Compo | Ammonium salt (mass %) | Reaction time (h) | T (° C.) | Conversion of citronellal (mole %) | % PMD in the organic phase at the end of the reaction (mole %) |
|---|---|---|---|---|---|
| 1.5 (1) | (B) (0.2%) | 6 h | 70° C. | 98 | 89 |
| 1.5 (2) | (B) (0.2%) | 6 h | 70° C. | 98 | 90 |
| 1.5 (3) | (B) (0.2%) | 6 h | 70° C. | 96 | 87 |
| 1.5 (4) | (B) (0.2%) | 6 h | 70° C. | 97 | 89 |
| 1.5 (5) | (B) (0.2%) | 6 h | 70° C. | 98 | 90 |
| 1.5 (6) | (B) (0.2%) | 6 h | 70° C. | 98 | 90 |
| 1.5 (7) | (B) (0.2%) | 6 h | 70° C. | 97 | 90 |
| 1.5 (8) | (B) (0.2%) | 6 h | 70° C. | 97 | 89 |

Example 2: Production of PMD from Essential Oils

Ammonium salts as defined according to the invention may also be used to convert the citronellal naturally present in an essential oil into PMD.

In order to do this, 2.5 mL of an essential oil are added to 10 mL of an aqueous solution comprising 0.4% by mass of an ammonium salt. The mixture is agitated for a period of 6 hours at 70° C., and then decanted. The PMD is comprised in the organic phase, and the aqueous phase includes the ammonium salt.

The results obtained are presented in the following table:

ratio in percentage of the amount of PMD obtained over the amount of citronellal converted.

When the ammonium salt used is the compound having the formula (B), the concentration of ammonium salt in aqueous solution may be decreased to 0.05% by mass.

Example 3: Behavioural Tests of *Aedes albopictus* vis-à-vis the Compositions of the Invention Testing was performed as to the activity of the compositions obtained by the method according to the invention on the behaviour of the tiger mosquito, *Aedes albopictus*.

The behavioural tests were carried out at the Montpellier Vectopôle, which is a research centre that collaborates with the WHO for the evaluation of insecticides in public health.

The tests were carried out on mosquitoes aged 5 to 9 days old after their evolution from pupae to adult.

In preparation for the experiment, the mosquitoes were fed sugar water only on the day prior thereto, in order to promote their appetite for the test to occur the subsequent day. Each test was carried out during the afternoon, the period during which the mosquitoes are most active.

Each cup contains a damp cotton. The female mosquitoes were removed from the cage making use of a tube that enables aspiration thereof. They were then introduced into each experiment cup (10 mosquitoes per cup).

The tests were carried out on plexiglass racks serving as supports for glass bells known as feeders. The latter are connected to each other by plastic pipes wherein water circulates at 37° C.

Pig intestinal skin was used to mimic human skin in the experiment. The pieces of intestinal skin are positioned and stretched over the feeders.

The repellent is diluted in ethyl alcohol (aka ethanol or EtOH) and is deposited on the skin using a micropipette and then spread over the entire surface. The concentration of commercial PMD is that of ED 50 (that is, the "median effective dose", which corresponds to the dose necessary for an active ingredient to produce a specific effect in 50% of a

TABLE 3

| | | | Composition of the organic phase at the end of the reaction | | | | | | | | |
|---|---|---|---|---|---|---|---|---|---|---|---|
| Compo | Ammonium salt | Essential oil | Linalool (mole %) | Citronellal (mole %) | Isopulegol (mole %) | Citronellol (mole %) | Geraniol (mole %) | Acetal (s) (mole %) | PMD (mole %) | Conversion (mole %) | Selectivity (mole %) |
| 2.1 | (H) | *Eucalyptus citriodora* | 0% | 1% | 11% | 3% | 0% | 2% | 82% | 99% | 85% |
| 2.2 | (G) | *Eucalyptus citriodora* | 0% | 10% | 12% | 3% | 0% | 3% | 72% | 90% | 83% |
| 2.3 | (V) | *Eucalyptus citriodora* | 0% | 8% | 13% | 3% | 0% | 2% | 74% | 92% | 84% |
| 2.4 | (B) | *Eucalyptus citriodora* | 0% | 1% | 7% | 3% | 0% | 1% | 88% | 99% | 91% |
| 2.5 | (H) | *Cymbopogon winterianus* | 3% | 1% | 4% | 15% | 29% | 0% | 48% | 98% | 92% |
| 2.6 | (G) | *Cymbopogon winterianus* | 2% | 4% | 4% | 15% | 30% | 0% | 45% | 92% | 92% |
| 2.7 | (V) | *Cymbopogon winterianus* | 1% | 15% | 3% | 14% | 31% | 0% | 36% | 73% | 91% |
| 2.8 | (B) | *Cymbopogon winterianus* | 1% | 9% | 2% | 13% | 30% | 0% | 45% | 93% | 96% |
| 2.9 | (H) | *Citrus hystrix* | 3% | 7% | 7% | 5% | 0% | 1% | 77% | 92% | 91% |
| 2.10 | (G) | *Citrus hystrix* | 3% | 10% | 7% | 5% | 0% | 1% | 74% | 89% | 91% |
| 2.11 | (V) | *Citrus hystrix* | 3% | 10% | 3% | 5% | 0% | 2% | 77% | 89% | 90% |
| 2.12 | (B) | *Citrus hystrix* | 3% | 10% | 3% | 5% | 0% | 2% | 77% | 89% | 93% |

The conversion rate corresponds to the percentage of citronellal comprised in the essential oil that reacted at the end of the reaction, and the selectivity corresponds to the population tested with that dose), which was established at 200 mg/m², tantamount to a concentration of 0.02036 mg/μL. If the composition tested is a mixture of at least two compounds, one of which is PMD, the said composition is diluted in ethanol until 0.02036 mg/μL of PMD is obtained.

The feeders are turned over, then 300 μL of sheep blood are placed in each feeder. The cups are inserted under each feeder.

Polystyrene plates are inserted between the lines of repellent so as to avoid possible interactions of odours. The duration of the experiment is one hour. The cups are then placed in a freezer at −20° C. for a period of 40 minutes. After freezing, the contents of one cup are placed between two sheets of paper, with the entirety thereof then being crushed with a plexiglass plate. The counting of the blood-fed (engorged) mosquitoes is done based on the number of red dots on the sheet of paper. The results are expressed as a percentage of repellency (100% −X% of blood-feeding). The percentage of blood-feeding is defined in relation to the EtOH negative control. DEET and commercial cis/trans PMD 75/25 at 200 mg/m² were used as positive controls.

The results obtained were statistically analysed using R software (R Development Core Team. R: A language and environment for statistical computing. R Foundation for Statistical Computing, Vienna, Austria. ISBN 3-900051-07-0, 2013) and represent the mean of 16 replicates. The percentage repellency values are presented as a mean±standard deviation. The R software also makes it possible to compare two percentage repellency values by means of calculating the quantity p. This quantity p is a probability. If $p<0.005$, the difference observed between the two compared values of percentage repellency is significantly different from a statistical standpoint.

Repellent Activity of the Compositions Obtained by the Method According to the Invention The repellent activity of the compositions obtained according to the method of the invention were tested on tiger mosquitoes according to the protocol described here above.

The results are presented in the following tables:

TABLE 4

| Repellent Composition | % Repellency |
|---|---|
| DEET (110 mg/m² in EtOH) (positive control) | 63 ± 5 |
| Commercial cis/trans PMD 75/25 (200 mg/m² in EtOH) (positive control) | 79 ± 4 |
| Composition 1.1 (200 mg/m² of PMD in EtOH) | 78 ± 3 |
| Composition 1.2 (200 mg/m² of PMD in EtOH) | 86 ± 5 |
| Composition 1.3 (200 mg/m² of PMD in EtOH) | 83 ± 4 |
| Composition 1.5 (200 mg/m² of PMD in EtOH) | 70 ± 7 |

The resulting compositions derived from the method according to the invention and obtained from pure citronellal (Example 1) are as active as the commercial cis/trans PMD 75/25.

TABLE 5

| Repellent Composition | % Repellency |
|---|---|
| DEET (110 mg/m² in EtOH) (positive control) | 49 ± 4 |
| Commercial cis/trans PMD 75/25 (200 mg/m² in EtOH) (positive control) | 59 ± 14 |
| PMD derived from the action of betaine on EO of *Eucalyptus citriodora* (Composition 2.4) (200 mg/m² of PMD in EtOH) | 71 ± 3 |

The Composition 2.4 is more active than commercial PMD (p=0.0044), and also exhibits a far greater efficacy than that of unmodified essential oil of *Eucalyptus citriodora* (% repellency=12%, p=0.00179). This result is particularly surprising, since the formation of PMD in the essential oil of *Eucalyptus citriodora* catalysed by citric acid as described in literature (Drapeau et al., C. R. Chimie 14 (2011) 629-635) does not lead to better repellency activity than that of commercial PMD (p=0.724). This result provides clear evidence of the interesting benefit of ammonium salt type catalysts.

TABLE 6

| Repellent Composition | % Repellency |
|---|---|
| DEET (110 mg/m² in EtOH) (positive control) | 49 ± 4 |
| Commercial cis/trans PMD 75/25 (200 mg/m² in EtOH) (positive control) | 68 ± 2 |
| PMD derived from the action of betaine on EO of *Cymbopogon winterianus* (Composition 2.8) (200 mg/m² of PMD in EtOH) | 55 ± 7 |

The Composition 2.8 and commercial PMD exhibit very similar repellant activities.

TABLE 7

| Repellent Composition | % Repellency |
|---|---|
| DEET (110 mg/m² in EtOH) (positive control) | 68 ± 10 |
| Commercial cis/trans PMD 75/25 (200 mg/m² in EtOH) (positive control) | 55 ± 10 |
| PMD derived from the action of betaine on EO of *Citrus hystrix* (Composition 2.12) (200 mg/m² of PMD in EtOH) | 77 ± 4 |

Composition 2.12 is as active as commercial PMD (p=0.1828). This result is innovative, because this essential oil has never been used as a raw material for preparing PMD.

Stereochemical Aspects—Comparisons of the Repellent Activity of Different Stereoisomers of PMD The repellent activity of compositions comprising various different commercial stereoisomers of PMD (cis or trans, or derived from the S or R enantiomer of citronellal) were tested on tiger mosquitoes according to the protocol described here above.

The results are presented in the following tables:

TABLE 8

| Repellent Composition | % Repellency |
|---|---|
| Commercial cis PMD (200 mg/m² in EtOH) | 64 ± 15 |
| Commercial trans PMD (200 mg/m² in EtOH) | 57 ± 6 |
| Commercial cis/trans PMD 60/40 (200 mg/m² in EtOH) | 68 ± 15 |
| Commercial cis/trans PMD 75/25 (200 mg/m² in EtOH) | 60 ± 5 |

TABLE 9

| Repellent Composition | % Repellency |
|---|---|
| DEET (110 mg/m² in EtOH) | 43 ± 1 |
| Commercial cis/trans PMD 75/25 (200 mg/m² in EtOH) derived from R citronellal | 24 ± 2 |
| Commercial cis/trans PMD 75/25 (200 mg/m² in EtOH) derived from S citronellal | 41 ± 3 |
| Commercial cis/trans PMD 75/25 (200 mg/m² in EtOH) derived from RS citronellal (racemic mixture) | 34 ± 1 |

These results demonstrate that there is no statistically significant difference between the cis PMD and trans PMD (p=0.86904), contrary to that which is shown in the work of Kraus (Lett, BD; Kraus, HS PCT Int. Appl. WO9202136, 1992; Chem. Abstr. 1992, 117, 2827).

In addition, there is no significant difference between the cis/trans PMD 75/25 and 60/40 ratios (p=0.735).

On the other hand, the stereoisomers of PMD derived from S citronellal are more active than those derived from R citronella (p=0.00397); however, they are not stastistically more active than those derived from racemic RS citronellal (p=0.485).

Combinatorial Chemoreception—Study of the Effects of Synergy between PMD and By-Products of Synthesis and/or Other Natural Terpenes Much of the work of the prior art is based on obtaining a PMD that is purified and isolated from the by-products of synthesis (the residual citronellal, isopulegol, the acetals resulting from the reaction between the PMD formed and the starting citronellal). However, for a given insect, the number of olfactory receptors is important. For example, *Aedes albopictus* has 138 olfactory receptors. Thus, a repellent molecule is recognised by several Olfactory Receptors (OR), and an OR recognises several odour molecules. The recognition is brought about by a process involving relative affinities with several ORs, and the information resulting therefrom is combinatorial in nature.

An experimental approach correlating composition with repellent activity was investigated in order to identify an interesting composition of a floral bouquet rich in PMD, which makes possible recognition of the signal leading to a repellent effect that is far greater than that of pure PMD. This approach is based on the concept of combinatorial chemoreception. This concept consists in finding the mixture of compounds that corresponds to the ideal combination with the targetted olfactory receptors.

The method is based on the following 2 steps:
  detecting the effects of synergy between PMD and the by-products of synthesis (citronellal, isopulegol, acetal (s)); and
  investigating the effects of synergy with other natural terpenes.

In the rest of the results, X% by mass (mass %) of a compound added to commercial PMD at 200 mg/m$^2$ signifies that the said compound was tested at a concentration of X*200 mg/m$^2$.

Effects of Synergy between PMD and By-Products of Synthesis (Acetal(s), Citronellal, Isopulegol)

The repellent activity of compositions comprising commercial PMD (cis/trans 75/25 mixture) alone or in a mixture with the acetals resulting from the reaction between citronellal and PMD, the citronellal or isopulegol, were tested on tiger mosquitoes according to the protocol described here above.

The results are presented in the following tables:

TABLE 10

| Repellent Composition | % Repellency |
| --- | --- |
| DEET (110 mg/m$^2$ in EtOH) | 41 ± 6 |
| Commercial cis/trans PMD 75/25 (200 mg/m$^2$ in EtOH) | 65 ± 8 |
| Commercial cis/trans PMD 75/25 (200 mg/m$^2$ in EtOH) + 4 mass % of acetal(s) | 79 ± 7 |
| Commercial cis/trans PMD 75/25 (200 mg/m$^2$ in EtOH) + 9 mass % of acetal(s) | 74 ± 5 |

The results show that the acetals present at 4 or 9% enhance the repellent activity of PMD (p=0.00305 and 0.0228 respectively).

TABLE 11

| Repellent Composition | % Repellency |
| --- | --- |
| DEET (110 mg/m$^2$ in EtOH) | 63 ± 8 |
| Commercial cis/trans PMD 75/25 (200 mg/m$^2$ in EtOH) | 69 ± 13 |
| Commercial cis/trans PMD 75/25 (200 mg/m$^2$ in EtOH) + 5 mass % of citronellal | 57 ± 9 |
| Commercial cis/trans PMD 75/25 (200 mg/m$^2$ in EtOH) + 12 mass % of citronellal | 74 ± 2 |

On the other hand, 5% citronellal or even 12% citronellal does not boost PMD activity (p=0.839 and 0.994 respectively). Given the irritant effects of this aldehyde at high concentrations, the study did not include any testing for citronellal above 12%.

TABLE 12

| Repellent Composition | % Repellency |
| --- | --- |
| DEET (110 mg/m$^2$ in EtOH) | 41 ± 6 |
| Commercial cis/trans PMD 75/25 (200 mg/m$^2$ in EtOH) | 63 ± 9 |
| Commercial cis/trans PMD 75/25 (200 mg/m$^2$ in EtOH) + 4 mass % of isopulegol | 72 ± 5 |
| Commercial cis/trans PMD 75/25 (200 mg/m$^2$ in EtOH) + 12 mass % of isopulegol | 71 ± 2 |

Finally, isopulegol may enhance the repellent activity of PMD (p=0.04847 with 4% isopulegol).

Effects of Synergy between PMD and Other Natural Terpenes

The olfactory receptors of *Aedes albopictus* are not yet all known.

Orientation tests in ElectroAntennogGraphy coupled with Gas Chromatography were carried out. The results of these tests showed that the stereoisomers of PMD, the citronellol, terpineol and caryophyllene are recognised at very low doses.

The repellent activity of compositions comprising commercial PMD (cis/trans 75/25 mixture) alone or in a mixture with terpineol or caryophyllene were tested on tiger mosquitoes according to the protocol described here above.

The results are presented in the following table:

TABLE 13

| Repellent Composition | % Repellency |
| --- | --- |
| DEET (110 mg/m$^2$ in EtOH) | 73 ± 7 |
| Commercial cis/trans PMD 75/25 (200 mg/m$^2$ in EtOH) | 59 ± 9 |
| Commercial cis/trans PMD 75/25 (200 mg/m$^2$ in EtOH) + 1 mass % of caryophyllene | 84 ± 8 |
| Commercial cis/trans PMD 75/25 (200 mg/m$^2$ in EtOH) + 1 mass % of terpineol | 90 ± 6 |

These results very clearly demonstrate that the presence of caryophyllene or terpineol enhances the repellent activity of PMD.

The repellent activity of compositions comprising commercial PMD (cis/trans 75/25 mixture) alone or in a mixture with citronellol, geraniol and terpineol were tested on tiger mosquitoes according to the protocol described here above.

The results are presented in the following table:

TABLE 14

| Repellent Composition | % Repellency |
|---|---|
| DEET (110 mg/m² in EtOH) | 28 ± 8 |
| Commercial cis/trans PMD 75/25 (200 mg/m² in EtOH) | 56 ± 13 |
| Commercial cis/trans PMD 75/25 (200 mg/m² in EtOH) + 5 mass % of citronellol + 21 mass % of geraniol + 1 ù mass % of terpineol | 80 ± 10 |

These results very clearly demonstrate that the presence of citronellol, geraniol and terpineol enhances the repellent activity of PMD.

The invention claimed is:

1. A method for preparing p-menthane-3,8-diol, comprising the following steps:
   a. preparing an aqueous solution comprising between 0.05% and 5% by mass of an ammonium salt, said ammonium salt being selected from the group consisting of an amino acid ammonium salt, a vitamin B ammonium salt, an ammonium salt of an amino acid ester, and an ammonium salt of a vitamin B ester, or is defined by the following formula (I):

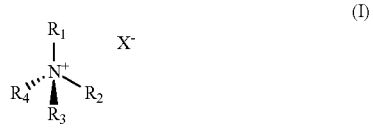

(I)

wherein $R_1$ represents a benzyl, optionally substituted, or $R_1$ represents an alkyl, either linear or branched, optionally cyclical, saturated or unsaturated, optionally substituted, comprising from 1 to 10 carbon atoms, and $R_2$, $R_3$ and $R_4$ represent a hydrogen or a methyl group, and X represents a chlorine atom, bromine atom or an OR' group, R' being an alkyl group comprising from 1 to 10 carbon atoms;
   b. adding of citronellal to the aqueous solution obtained in the step a), and obtaining a mixture;
   c. stirring and heating of the mixture obtained in the step b);
   d. decanting of the reaction medium obtained at the end of step c) and obtaining at least two phases; and
   e. separating said at least two phases obtained in the step d), to obtain at least one aqueous phase and at least one organic phase, said organic phase comprising at least p-menthane-3,8-diol.

2. The method according to claim 1, wherein the amino acid ammonium salt derivative comprises at least one COOR ester functional group, R being an alkyl, either linear or branched, comprising from 1 to 10 carbon atoms.

3. The method according to claim 1, wherein the amino acid ammonium salt is selected from the group consisting of hydrochlorides of histidine, guanine and glycine.

4. The method according to claim 1, wherein the group R1 is a saturated linear alkyl group, comprising from 1 to 10 carbon atoms, and further comprising a carboxylic acid functional group.

5. The method according to claim 1, wherein the ammonium salt is selected from the group consisting of O-methylated histidine dihydrochloride, guanine hydrochloride, O-methylated glycine hydrochloride, vitamin B1 dihydrochloride, vitamin B6 hydrochloride, and 2-trimethylammonioacetate hydrochloride.

6. The method according to claim 1, wherein the citronellal is used in the form of an essential oil.

7. The method according to claim 1 wherein the organic phase obtained at the end of step e) further comprises at least one compound selected from the group consisting of citronellal, isopulegol and an acetal, said acetal being produced by reaction between citronellal and p-menthane-3,8-diol.

8. The method according claim 1, wherein the organic phase obtained at the end of step e) further comprises at least one compound selected from the group consisting of linalool, citronellol and geraniol.

9. The method according to claim 1, wherein the method further comprises a step f) of adding at least one compound selected from the group consisting of citronellol, geraniol, terpineol and caryophyllene to the organic phase comprising p-menthane-3,8-diol obtained in the step e).

10. A composition obtained by the method according to claim 1, comprising: at least 70 mole % of p-menthane-3,8-diol relative to the total number of moles of the composition; citronellal and an acetal; and optionally isopulegol; said acetal being produced by reaction between citronellal and p-menthane-3,8-diol.

11. The composition according to claim 10, wherein the composition comprises from 70 to 98 mole % of p-menthane-3,8-diol.

12. The composition according to claim 10, wherein the composition comprises, relative to the total number of moles of the composition:
   from 70 to 98 mole % of p-menthane-3,8-diol;
   from 0.1 to 40 mole % of citronellal;
   from 0.1 to 20 mole % of acetal; and optionally
   from 1 to 30 mole % of isopulegol.

13. The composition according to claim 10, wherein the composition further comprises from 0.1 to 10 mole % of terpineol.

14. The composition according to claim 10, wherein the composition further comprises from 0.1 to 10 mole %.

15. The composition according to claim 10, wherein the composition further comprises from 0.1 to 15 mole % of linalool.

16. The composition according to claim 10, wherein the composition further comprises from 0.1 to 40 mole % of citronellol.

17. The composition according to claim 10, wherein the composition further comprises from 0.1 to 40 mole % of geraniol.

18. Method of repelling at least one hematophagous arthropod from a target of the hematophagous arthropod, comprising applying on said target the composition according to claim 10.

19. The method according to claim 18, wherein the hematophagous arthropod is selected from the group consisting of mosquitoes, ticks and midges.

20. The method according to claim 18, wherein the hematophagous arthropod is a mosquito.

* * * * *